United States Patent
Emerson

(10) Patent No.: US 6,929,007 B2
(45) Date of Patent: Aug. 16, 2005

(54) INSUFFLATION-EXSUFFLATION SYSTEM WITH PERCUSSIVE ASSIST FOR REMOVAL OF BRONCHO-PULMONARY SECRETIONS

(75) Inventor: George P. Emerson, Arlington, MA (US)

(73) Assignee: J.H. Emerson Company, Cambridge, MA (US)

(*) Notice: Subject to any disclaimer, the term of this patent is extended or adjusted under 35 U.S.C. 154(b) by 169 days.

(21) Appl. No.: 10/657,424

(22) Filed: Sep. 8, 2003

(65) Prior Publication Data
US 2005/0051174 A1    Mar. 10, 2005

(51) Int. Cl.$^7$ .............................................. A62B 7/10
(52) U.S. Cl. ..................... 128/205.12; 128/204.23; 482/13
(58) Field of Search ............... 128/204.21, 204.23, 128/204.26, 205.12, 205.19; 600/41–43; 482/13

(56) References Cited

U.S. PATENT DOCUMENTS

| | | | |
|---|---|---|---|
| 1,044,031 A | 11/1912 | Dräger | 128/205.19 |
| 1,169,995 A | 2/1916 | Prindle | 128/205.19 |
| 1,358,893 A | 11/1920 | Eugen | 128/204.25 |
| 2,364,626 A | 12/1944 | Emerson | 128/204.25 |
| 2,428,451 A | 10/1947 | Emerson | 128/205.13 |
| 2,468,741 A | 5/1949 | Emerson | 128/204.25 |
| 2,481,299 A | 9/1949 | Emerson | 128/204.25 |
| 2,512,621 A * | 6/1950 | Emerson | 601/58 |
| 2,774,347 A | 12/1956 | Emerson | 601/43 |
| 2,774,348 A | 12/1956 | Emerson | 601/43 |
| 2,853,998 A | 9/1958 | Emerson | 601/44 |
| 2,861,568 A | 11/1958 | Cuthbert et al. | 128/201.23 |
| 2,914,064 A | 11/1959 | Sandelowsky | 128/205.19 |
| 2,918,917 A * | 12/1959 | Emerson | 128/205.19 |
| 3,357,428 A | 12/1967 | Carlson | 128/204.23 |
| 3,368,212 A | 2/1968 | Klyce, Jr. | 340/606 |
| 3,402,711 A | 9/1968 | Emerson | 128/204.28 |
| 3,653,379 A * | 4/1972 | Glenn | 128/204.21 |
| 3,768,468 A | 10/1973 | Cox | 128/204.21 |
| 3,794,026 A | 2/1974 | Jacobs | 128/200.13 |
| 3,850,170 A | 11/1974 | Cox | 128/204.24 |
| 3,976,064 A | 8/1976 | Wood et al. | 128/204.21 |
| 4,054,134 A * | 10/1977 | Kritzer | 128/205.24 |
| 4,062,358 A * | 12/1977 | Kritzer | 128/205.24 |
| 4,193,406 A | 3/1980 | Jinotti | 128/204.18 |
| 4,206,754 A | 6/1980 | Cox et al. | 128/204.21 |
| 4,273,120 A | 6/1981 | Oswell | 128/204.26 |
| 4,281,651 A | 8/1981 | Cox | 128/204.23 |
| 4,393,869 A | 7/1983 | Boyarsky et al. | 128/204.18 |
| 4,565,194 A | 1/1986 | Weerda et al. | 128/204.23 |
| 4,592,741 A * | 6/1986 | Vincent | 604/35 |
| 4,595,004 A * | 6/1986 | Czech | 128/204.21 |
| 4,977,889 A * | 12/1990 | Budd | 601/44 |
| 5,127,398 A | 7/1992 | Stone | 128/204.18 |

(Continued)

Primary Examiner—Aaron J. Lewis
(74) Attorney, Agent, or Firm—Iandiorio & Teska

(57) ABSTRACT

An improved insufflation-exsufflation system with percussive assist for removal of broncho-pulmonary secretions includes a conduit for connection to a patient's airway; a pressure source for providing to the conduit alternating positive and negative pressure fluctuations at a first rate corresponding to patient insufflation-exsufflation; and a control mechanism for varying pressure during positive and negative pressure fluctuations at a second higher rate to periodically decrease the positive pressure during positive fluctuations and decrease the negative pressure during negative fluctuations to provide percussive pulses during at least one of insufflation-exsufflation to clear broncho-pulmonary secretions from the patient's airway.

10 Claims, 4 Drawing Sheets

U.S. PATENT DOCUMENTS

| | | | | |
|---|---|---|---|---|
| 5,280,784 A | * | 1/1994 | Kohler | 128/200.14 |
| 5,311,862 A | | 5/1994 | Blasdell et al. | 128/205.25 |
| 5,400,778 A | | 3/1995 | Jonson et al. | 128/205.19 |
| 5,419,768 A | | 5/1995 | Kayser | 604/119 |
| 5,611,335 A | * | 3/1997 | Makhoul et al. | 128/204.24 |
| 5,645,537 A | * | 7/1997 | Powles et al. | 604/240 |
| 5,673,689 A | | 10/1997 | Power | 128/205.18 |
| 5,829,429 A | * | 11/1998 | Hughes | 128/200.24 |
| 5,850,835 A | | 12/1998 | Takaki et al. | 128/204.18 |
| 5,893,361 A | * | 4/1999 | Hughes | 128/200.24 |
| 5,988,166 A | | 11/1999 | Hayek | 128/205.26 |
| 6,058,932 A | * | 5/2000 | Hughes | 128/200.24 |
| 6,167,881 B1 | * | 1/2001 | Hughes | 128/200.24 |
| 6,176,235 B1 | * | 1/2001 | Benarrouch et al. | 128/200.24 |
| 6,209,540 B1 | | 4/2001 | Sugiura et al. | 128/204.18 |
| 6,547,749 B2 | * | 4/2003 | Hansen | 601/48 |
| 6,595,213 B2 | | 7/2003 | Bennarsten | 128/205.19 |
| 6,694,978 B1 | * | 2/2004 | Bennarsten | 128/204.21 |

* cited by examiner

INSUFFLATION-EXSUFFLATION SYSTEM WITH PERCUSSIVE ASSIST FOR REMOVAL OF BRONCHO-PULMONARY SECRETIONS

FIELD OF THE INVENTION

This invention relates to an improved insufflation-exsufflation system with a percussive assist for removal of broncho-pulmonary secretions during at least one of insufflation and exsufflation.

BACKGROUND OF THE INVENTION

The use of mechanical insufflation and exsufflation (MI-E) with negative pressure is a well-known technique for helping patients with an ineffective cough to remove secretions from the respiratory tract. Patients who can benefit from the technique include: post-polio, muscular dystrophy, spinal muscular atrophy (SMA), post-cardiac surgery, amyotropic lateral sclerosis (ALS), mechanically ventilated, or anyone with insufficient muscle strength to generate the high expiratory flows necessary for moving secretions up the tracheo-bronchial tree. The technique involves the use of a blower and valve, which via a facemask, mouthpiece or adapter for a tracheal tube, alternately applies positive pressure first to inflate the lungs, then shifts rapidly to negative pressure to create a high expiratory flow. One shortcoming of MI-E is its limited effectiveness on patients with unusually thick or tenacious secretions. In such patients MI-E can create high expiratory airflows, but the secretions tend to remain attached to the airways within the lung and cannot be dislodged or loosened.

The use of percussion in loosening secretions in patients' airways is also a well-known technique. The most widely used is referred to as "chest physical therapy", wherein a nurse or physical therapist uses cupped hands to rhythmically strike the chest wall, producing vibrations in the lung tissue. There are also devices that accomplish this percussion both external to the body via mechanical "thumpers" or positive pressure vests, and internally via a facemask or mouthpiece, using short bursts of positive pressure to the airway. In addition, some devices, like the "Flutter®" (Axcan Scandipharm) and the "Acapella®V" (DHD Healthcare) use the patient's own expiratory flow to generate oscillations in the airway.

A shortcoming of these various percussive techniques is that they effectively loosen secretions in a patient's airways, but do not actively remove the secretions, as does MI-E. In fact, for a patient with insufficient peak cough expiratory flow, the use of percussion alone may loosen a mucus plug, which the patient cannot expel, causing blockage of the airway. Also, patients with neuromuscular disease or general muscle weakness cannot generate adequate airflow to use the "Flutter®" or "Acapella®" devices.

One approach, U.S. Pat. No. 2,918,917, applies a vibration to either a positive pressure, (inhale), or negative pressure, (exhale) but not both. This has not been satisfactory in some applications. Also this approach employs a diaphragm pump to fluctuate the air provided to the patient. Such pumps are large and not conducive to portability and require significant energy in addition to that used to drive the primary pressure source. In addition, in applying pressure oscillations this approach must work against the pressures provided by the primary pressure source itself.

BRIEF SUMMARY OF THE INVENTION

It is therefore an object of this invention to provide an improved insufflation-exsufflation system.

It is a further object of this invention to provide such an improved insufflation-exsufflation system which provides a percussive assist for removal of broncho-pulmonary secretions.

It is a further object of this invention to provide such an improved insufflation-exsufflation system which provides percussive pulse assists during either or both positive pressure fluctuations and negative pressure fluctuations.

It is a further object of this invention to provide such an improved insufflation-exsufflation system which provides percussive pulse assists simultaneously with insufflation and exsufflation (positive and negative pressure fluctuations, respectively) of the patient.

It is a further object of this invention to provide such an improved insufflation-exsufflation system which is smaller, more portable and more economical of energy.

The invention results from the realization that an improved insufflation-exsufflation system with percussive assist for removal of broncho-pulmonary secretions can be effected by providing alternating positive and negative pressure fluctuations at a first rate corresponding to patient insufflation and exsufflation and varying the pressure during positive and negative pressure fluctuations at a second higher rate to periodically decrease the positive pressure during positive fluctuations and decrease the negative pressure during negative fluctuations to provide percussive pulses during at least one of insufflation and exsufflation to clear broncho-pulmonary secretions from a patient's airway.

This invention features an improved insufflation-exsufflation system with percussive assist for removal of broncho-pulmonary secretions. There is a conduit for connection to a patient's airway and a pressure source for providing to the conduit alternating positive and negative pressure fluctuations at a first rate corresponding to patient insufflation and exsufflation. A control mechanism varies the pressure during positive and negative pressure fluctuations at a second higher rate to periodically decrease the positive pressure during positive fluctuations and decrease the negative pressure during negative fluctuations to provide percussive pulses during at least one of insufflation and exsufflation to clear broncho-pulmonary secretions from the patients airways.

In a preferred embodiment the control mechanism may include a valve device. The valve device may vent the positive and negative pressure provided by the air pressure source to generate the positive and negative pressure pulses. There may be a flow control device for setting the level of pressure decreases during the pulses. The flow control device may include a restrictor mechanism. There may be a drive device for controlling the frequency of the second rate. The drive device may include a motor and a motor drive circuit. The valve may have an open position for generating the pressure pulses and a closed position. The valve may have a partially closed position for reducing the overall pressure of the pressure fluctuations produced by the pressure source in the conduit and an open position for generating the percussive pulses. There may be a drive circuit for controlling at least one of the frequency and stroke of the valve.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Figure 1:
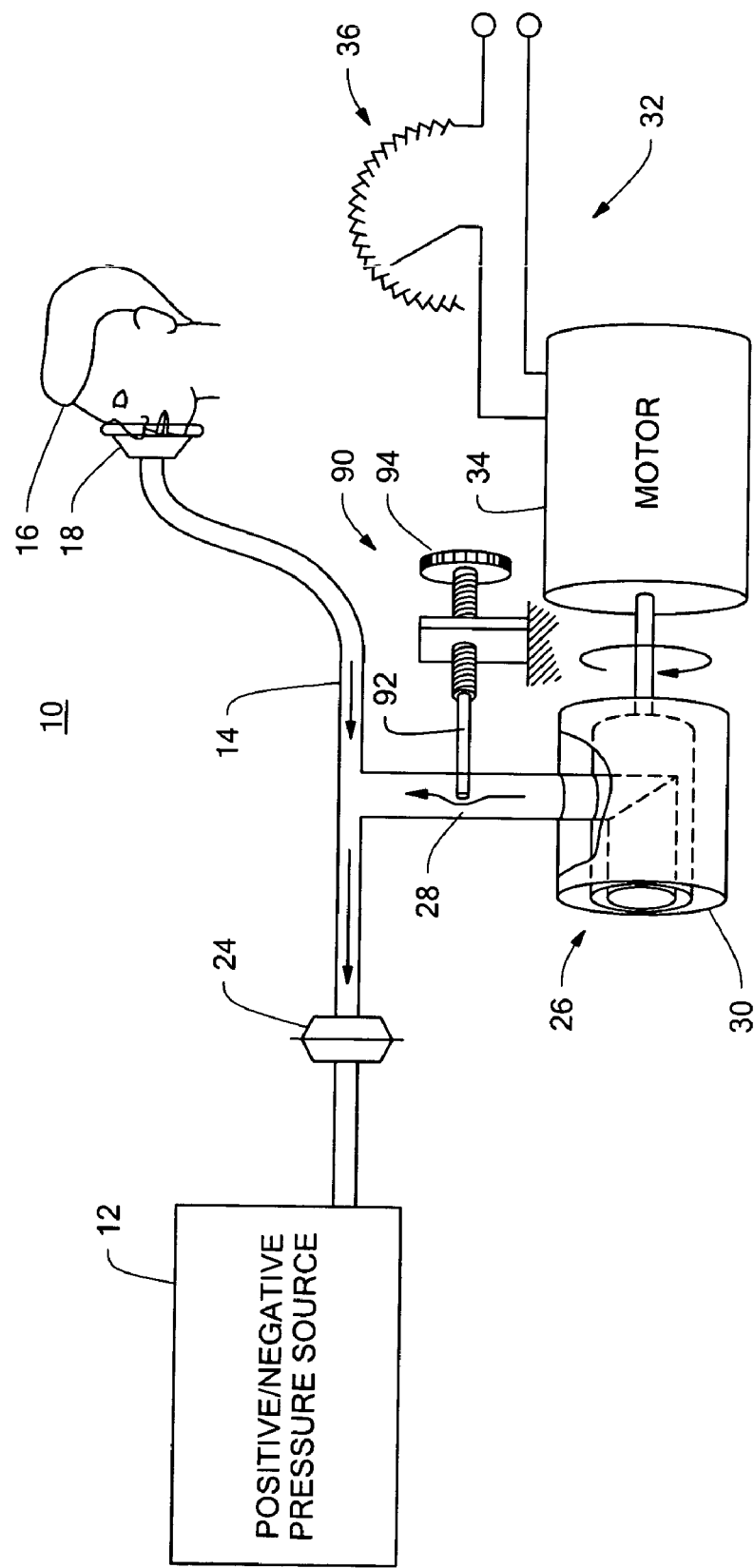
FIG. 1 is a schematic block diagram of an insufflation-exsufflation system according to this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

Figure 2:
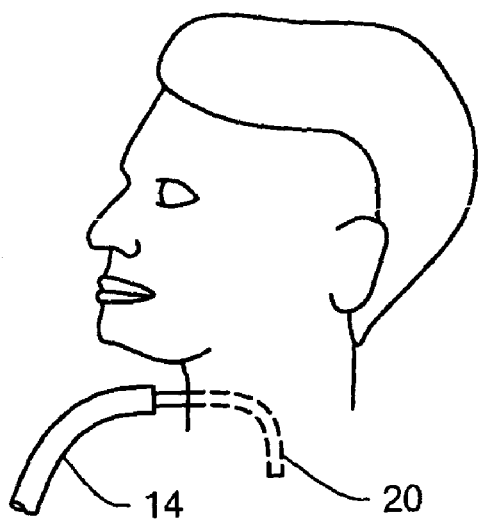
FIGS. 2 and 3 are schematic diagrams showing alternative connections of the system to a patient's airway.
Figure 3:
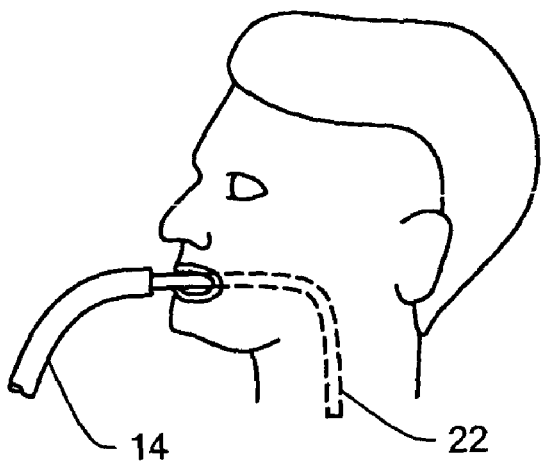
Figure 4:
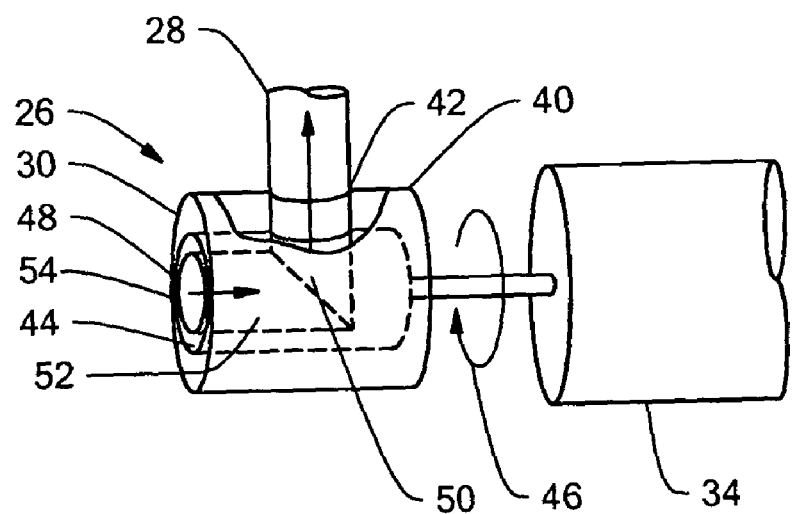
FIG. 4 is an enlarged detail view of the percussive control mechanism of FIG. 1.

There is shown in FIG. 1 an improved insufflation-exsufflation system 10, with percussive assist for removal of broncho-pulmonary secretions according to this invention including a positive/negative pressure source 12 and a conduit 14 for supplying air to and withdrawing air from a patient 16 via a face mask 18 which covers the patient's nose and mouth. Alternatively, conduit 14 may be engaged with a trachostomy tube 20, FIG. 2, or with an endotracheal tube 22, FIG. 3. A bacterial filter 24 is typically included someplace in the conduit. A percussive control mechanism includes conduit 28 and a valve device 30 operated by a drive device 32 which may include motor 34 and a motor drive circuit 36. Valve 30, FIG. 4, of valve device 26 includes an outer stationary portion 40, FIG. 4, containing port 42 that engages with conduit 28 and a rotor 44 driven by shaft 46 of motor 34. Rotor 44 includes a right angle channel 48 which includes a radial portion 50 that aligns with port 42 once each revolution and an axial portion 52 which is open to the atmosphere at its end 54. Thus as shaft 46 rotates by means of motor 34 rotor 44 rotates as well disengaging channel 50 from port 42 through the entire rotation except at the position where it aligns with conduit 28.

Figure 5:
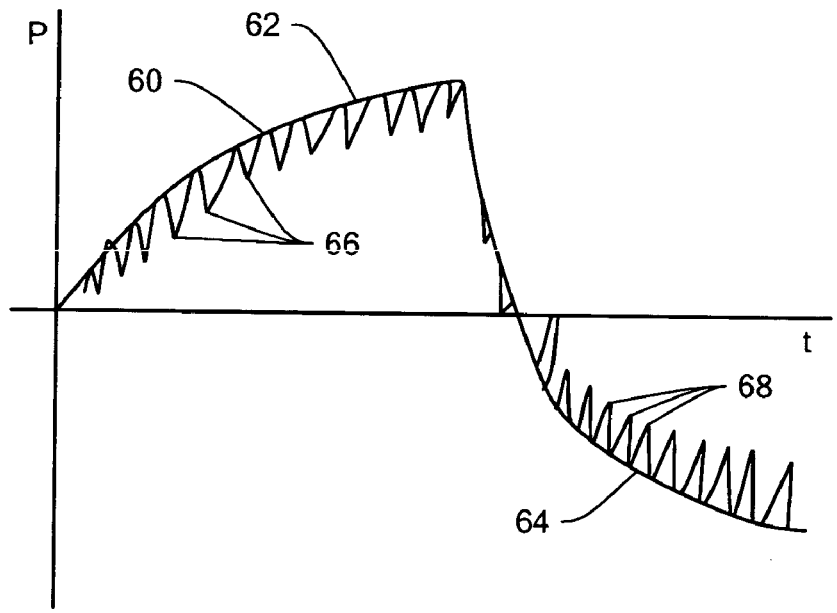
FIG. 5 is a waveform illustrating the positive and negative pressure fluctuations with the modulating percussive pulses superimposed thereon.

In operation as can be seen in FIG. 1, this vents the positive and negative pressure provided by pressure source 12 in conduit 14. The faster motor 34 rotates the more times the pressure and conduit 14 will be vented. The effect can be seen more readily in FIG. 5, where the primary pressure cycle is shown as consisting of a positive pressure fluctuation 62 followed by a negative pressure fluctuation 64 that is, the insufflation-exsufflation or inhale-exhale, respectively, periods of operation. During each of the positive and negative fluctuations 62 and 64 the venting, by means of valve 30 and motor 34, provides sharp percussive pulses 66 which momentarily decrease the positive pressure during positive pressure fluctuation 62 and creates similar percussive pulses 68 which reduce the negative pressure during negative pressure pulse 64. The combination of this continuous insufflation-exsufflation cycle of the primary positive pressure and negative pressure fluctuation 62 and 64 accompanied by the percussive pulses 66 and 68 provides an extremely effective, safe and comfortable means for simultaneously loosening and withdrawing secretions from the patient's airway. The invention applies as well to percussive pressure applied to at least one of insufflation and exsufflation.

Figure 6:
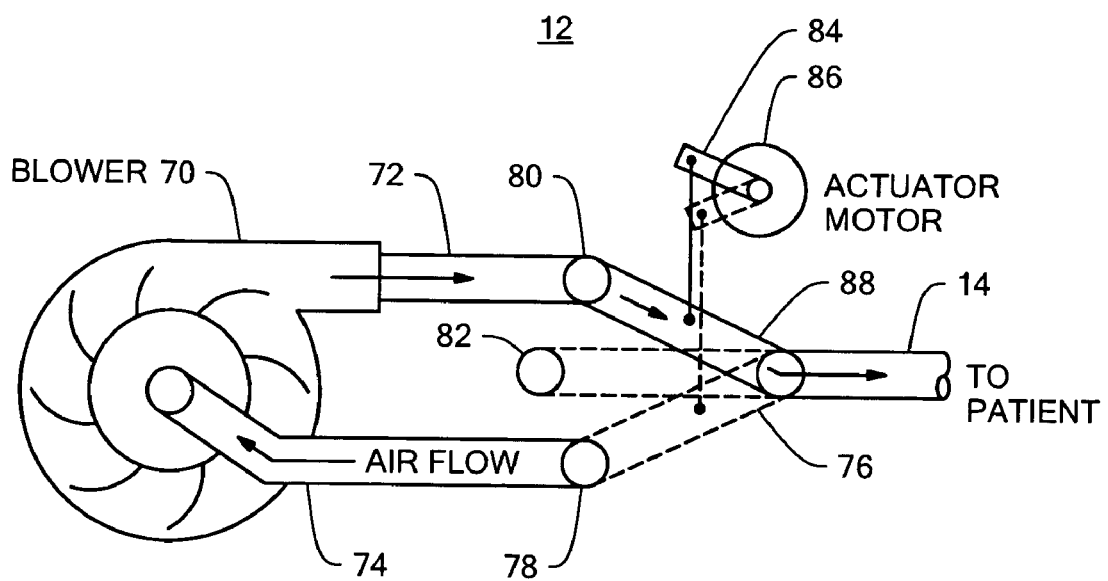
FIG. 6 is a more detailed schematic diagram of the positive/negative pressure source of FIG. 1.
Figure 7:
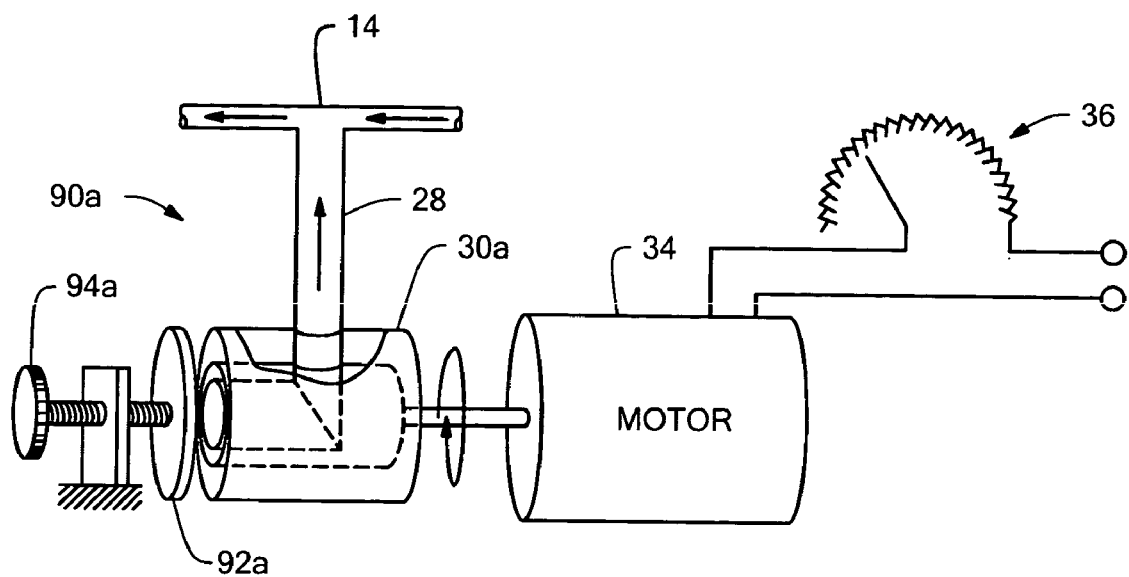
FIG. 7 is a schematic diagram of an alternative percussive control mechanism for FIG. 1.

Positive/negative source 12, FIG. 6, may include a conventional blower 70 having a positive or inhale output for insufflation 72 and a negative 74 or exhale output for exsufflation. A three position slide valve 76 includes a negative port 78 positive port 80 and a dwell port 82 which is typically connected to atmospheric pressure. Eccentric mechanism 84 driven by motor 86 in a conventional manner moves swinger 88 from positive port 80 to negative port 78, to dwell port 82, back to positive port 80 and so on. While the frequency of the percussive pulses is determined by the speed of motor 34 the magnitude of those pulses can be controlled using a flow control device 90 which may include a restrictor valve 92 and some means of adjustment, such as thumb screw 94 which controls the amount of air which will be vented each cycle of valve 30. The restricting function may also be accomplished by means of a flow control device 90a, FIG. 7, which employs a cap plate 92a that can be moved to and fro along the longitudinal axis of valve 30a by means of thumb screw 94a.

Figure 8:
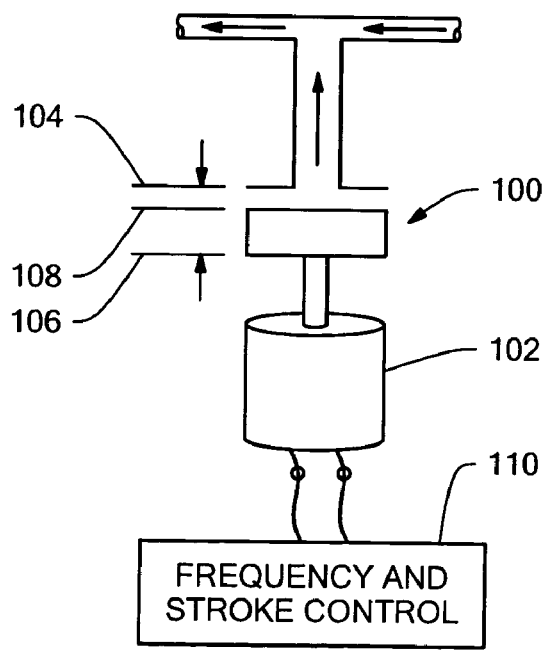
FIG. 8 is a schematic diagram of another alternative percussive control mechanism usable with FIG. 1.

In another embodiment a poppet type valve, 100, FIG. 8, may be operated by a linear actuator 102 between a closed position 104 and an open position 106 for providing the percussive pulses. Alternatively, poppet valve 100 may function as both a generator of percussive pulses and a control for the overall pressure provided by pressure source 12 and conduit 14. In that capacity poppet valve 100 would move between an open position 106 and a partially closed position 108 so that a portion of the pressure is always bled off when the valve is in the partially closed position 108 and then even more is bled off at open position 106 to create the percussive pulses. A frequency and stroke control circuit 110 is used to control the frequency of oscillation of poppet valve 100 as well as the distance of its stroke.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims.

What is claimed is:

1. An improved insufflation-exsufflation system with percussive assist for removal of broncho-pulmonary secretions comprising:
   a conduit for connection to a patient' airway;
   a pressure source for providing to said conduit alternating positive and negative pressure fluctuations at a first rate corresponding to patient insufflation and exsufflation; and
   a control mechanism for varying pressure during positive and negative pressure fluctuations at a second higher rate to periodically decrease the positive pressure during positive fluctuations and decrease the negative pressure during negative fluctuations to provide percussive pulses during at least one of insufflation and exsufflation to clear broncho-pulmonary secretions from the patient's airway.

2. The improved insufflation-exsufflation system of claim 1 in which said control mechanism includes a valve device.

3. The improved insufflation-exsufflation system of claim 2 in which said valve device vents the positive and negative pressure provided by said pressure source to generate the positive and negative pressure pulses.

4. The improved insufflation-exsufflation system of claim 2 in which said valve has an open position for generating said pressure pulses and a closed position.

5. The improved insufflation-exsufflation system of claim 2 in which said valve has a partially closed position for reducing the overall pressure of the pressure fluctuations produced by said pressure source in said conduit and an open position for generating said pressure pulses.

6. The improved insufflation-exsufflation system of claim 5 further includes a drive circuit for controlling at least one of the frequency and stroke of said valve.

7. The improved insufflation-exsufflation system of claim 1 further includes a flow control device for setting the level of pressure decreases during said pulses.

8. The improved insufflation-exsufflation system of claim 7 in which said flow control device includes a restriction mechanism.

9. The improved insufflation-exsufflation system of claim 1 further including a drive device for controlling the frequency of said second rate.

10. The improved insufflation-exsufflation system of claim 9 in which said drive device includes a motor and a motor drive circuit.

* * * * *